(12) United States Patent
Fernyhough

(10) Patent No.: US 7,883,511 B2
(45) Date of Patent: Feb. 8, 2011

(54) METHOD AND COMPOSITION FOR USE IN REINFORCING BONE

(76) Inventor: Jeffrey C. Fernyhough, 144 Alexander Palm Rd., Boca Raton, FL (US) 33432

( * ) Notice: Subject to any disclaimer, the term of this patent is extended or adjusted under 35 U.S.C. 154(b) by 206 days.

(21) Appl. No.: 11/854,226

(22) Filed: Sep. 12, 2007

(65) Prior Publication Data

US 2009/0069815 A1 Mar. 12, 2009

(51) Int. Cl.
*A61B 19/00* (2006.01)
*A61F 13/02* (2006.01)

(52) U.S. Cl. .................... 606/92; 606/86 R; 606/93; 606/94

(58) Field of Classification Search .............. 606/60, 606/62, 76, 77, 86, 92–94; 128/897, 898; 623/16.11, 17.11, 18.11, 11.11, 22.11
See application file for complete search history.

(56) References Cited

U.S. PATENT DOCUMENTS

| | | | |
|---|---|---|---|
| 5,334,626 A | | 8/1994 | Lin |
| 5,343,877 A | * | 9/1994 | Park .................... 128/898 |
| 5,398,483 A | | 3/1995 | Smith et al. |
| 5,795,922 A | | 8/1998 | Demian et al. |
| 6,048,346 A | | 4/2000 | Reiley et al. |
| 6,241,734 B1 | | 6/2001 | Scribner et al. |
| 6,582,439 B1 | | 6/2003 | Sproul |
| 6,726,691 B2 | | 4/2004 | Osorio et al. |
| 6,949,251 B2 | | 9/2005 | Dalal et al. |
| 6,979,352 B2 | | 12/2005 | Reynolds |
| 7,008,433 B2 | | 3/2006 | Voellmicke et al. |
| 2003/0032964 A1 | | 2/2003 | Watkins et al. |
| 2003/0220648 A1 | | 11/2003 | Osorio et al. |
| 2004/0052829 A1 | | 3/2004 | Shimp |
| 2004/0092946 A1 | | 5/2004 | Bagga et al. |
| 2004/0167562 A1 | | 8/2004 | Osorio et al. |
| 2005/0251149 A1 | | 11/2005 | Wenz |
| 2005/0257714 A1 | | 11/2005 | Constantz et al. |
| 2005/0287071 A1 | | 12/2005 | Wenz |
| 2006/0052743 A1 | | 3/2006 | Reynolds |
| 2006/0122614 A1 | | 6/2006 | Truckai et al. |
| 2007/0185231 A1 | * | 8/2007 | Liu et al. .................... 523/116 |
| 2007/0208295 A1 | * | 9/2007 | Oloodmiyazdi .............. 604/82 |

OTHER PUBLICATIONS

Srikumaran, Umasuthan, Wade Wong, Stephen M. Belkoff and Edward F. McCarthy, Histopathologic Analysis of Human Vertebral Bodies After Vertebral Augmentation with Polymethylmethacrylate with Use of an Inflatable Bone Tamp. A Case Report, The Journal of Bone and Joint Surgery Am.87:1838-1843, 2005. doi: 10.2106/JBJS.D.02848, Needham, MA.

\* cited by examiner

*Primary Examiner*—Thomas C Barrett
*Assistant Examiner*—Sameh Boles
(74) *Attorney, Agent, or Firm*—McHale & Slavin, P.A.

(57) ABSTRACT

The invention provides a method and a kit for administering bone cement to the interior cavity of a bony member to enhance bone strength, stabilizing an existing fracture thus reducing susceptibility of the bone to further fracture and/or collapse. The method and kit may include additional components, such as, bone growth enhancing agents, radiopaque components or the like.

14 Claims, 3 Drawing Sheets

METHOD AND COMPOSITION FOR USE IN REINFORCING BONE

FIELD OF THE INVENTION

This invention relates generally to a method and kit useful for reinforcing and stabilizing bones; particularly, to administration of bone cement to the interior cavity of fractured and/or diseased bone for enhanced strength providing stabilization of bone fractures and/or reduction of collapse.

BACKGROUND OF THE INVENTION

Bones provide support for muscle movement and protection for organs. Living bone tissue is in a constant state of flux due to the process of bone remodeling. The bone matrix is continuously deposited and resorbed. This rapid turnover of bone occurs throughout childhood as bones increase in size, density, and thickness until the individual reaches a genetically-determined adult height. Once at adult height, bones cease to grow in size but continue to increase in thickness until the individual reaches approximately 30 years of age. As bone growth ceases, the bone is resorbed faster than it is replaced, thus leading to a gradual thinning of the bones. The thinning bone tissue deteriorates and creates spaces or pores between the units of the bony matrix. This process is commonly referred to as osteoporosis.

Osteoporosis is characterized by increased fragility of bones resulting from the loss of bone tissue from the interior of the bone tissue (cancellous bone tissue). Such bone loss reduces the overall density of the internal bone tissue (osteopenia). Thus, both cancellous bone tissue and the surrounding cortical bone can both easily fracture/collapse from even minimal trauma. For example, when a vertebral body fractures, it collapses, and may allow the spine to deform collapsing forward and also reducing its overall length. Vertebral body collapse/fractures (VCFs) can cause serious side effects with patients suffering acutely from loss of height, severe localized pain from the loss of structural stability or more chronic long term pain and problems from the resulting secondary developing kyphosis or scoliosis deformity, and from the postural deformity or the resulting chronic instability of the fracture or even increased pressure on the spinal nerves, stretching of muscles, tendons, and ligaments by the misshapen spinal deformity. Often the osteoporotic patient experiences decreased mobility leading to an inability to carry out everyday tasks and overall reduction in quality of life. Obviously, preventing bone loss would significantly improve the health, well-being, and functional capabilities of the patient. Osteoporosis or other bone-related diseases and/or defects can also affect long bones. Significant osteopenia and focal bone destruction may also result from other sources, such as, cancer, destructive tumors, infections, radiation treatments, hemangiomas, corticosteroid regimens, etc.

Osteoplasty refers to any surgical procedure or process by which total or partial loss of bone is remedied. Continuing with the vertebral body example, vertebroplasty and KYPHOPLASTY represent two recently developed minimally invasive osteoplastic procedures for repairing and stabilizing vertebral body collapse/fracture (VCFs) by injecting a flowable hardening material (surgical cement system), usually into the interior (medullary) cavity of a fractured or otherwise damaged vertebral body, usually under image-guided control (fluoroscopic, CT Scan, etc.) The cement material solidifies in situ, thereby stabilizing the fracture, which relieves pain and prevents further collapse of the vertebral body. Vertebroplasty involves the percutaneous injection of the flowable cement into the targeted vertebral body via a delivery means (e.g., trocar, needle, lumen or cannula). Significant correction of the spinal collapse and reconstitution of pre-fracture vertebral height as well as kyphosis correction occurs with spinal positioning on the table into a neutral or lordotic posture in preparation for the vertebroplasty procedure in those fractures which are unstable and still mobile.

KYPHOPLASTY is a surgical procedure similar to vertebroplasty which includes attempted restoration of vertebral height by inflation of a balloon within the interior vertebral body creating a cavity prior to injection of the hardening cement material. This attempts to gain better control of the size and shape of the interior cavity and the resultant size and shape of the cement. Unfortunately with KYPHOPLASTY the cement is limited by the low pressure injection into the void created by the balloon deployment. And therefore does not commonly permeate well into the remaining, adjacent osteoporotic bone and the adjacent subchondral region, leaving it susceptible to further fracture collapse later with weight bearing. As discussed above, the cement ostensibly provides stabilization, or internal casting of VCFs. In both of the aforementioned procedures the cement is inserted under variable pressure by mechanical, electrical, or manual insertion means (e.g., pumps). Substantially less pressure being utilized by the KYPHOPLASTY procedure. Unfortunately KYPHOPLASTY procedure requires much more expensive equipment, larger needles, and implants for the technique which are much more complex and involved and time consuming to perform with insertion of an expandable balloon device which creates a cavity to inject the cement into, under less pressure, purportedly with less cement extravasation. The act of balloon inflation also unfortunately can cause the surrounding intact osteoporotic cancellous bone to fracture further as the intended void is created—to fill with the cement. Increased pain is often experienced later as this newly fractured bone may collapse around the cement. Furthermore there is very little if any permeation and penetration of bone cement into the remaining vertebral osteoporotic body or subchondral endplate level to stabilize this already weakened bone and prevent further fracture and collapse later; clearly a significant benefit of the higher injection pressures utilized with the vertebroplasty procedure.

After injection, the surgical cement material solidifies thereby providing support and reinforcement to the collapsing, fractured bone (e.g. vertebral body) internally. This support restores structural stability to the fractured bone and relieves the compression fracture pain of instability, or deformation of the vertebral body and the pain associated with the kyphosis deformity and/or instability of the fracture. These procedures are monitored by an imaging system to identify extravasation (leakage) of the cement material through cracks and/or gaps in the cancellous and/or cortical bone to the area surrounding the vertebral body or into the spinal canal prior to curing. The incidence of cement extravasation is usually higher in vertebroplasty procedures than the comparative rates in KYPHOPLASTY procedures however it has been shown to be only rarely clinically significant. The injection of cement is usually terminated if extravasation is identified or appears imminent by the radiographic imaging used to monitor the cement flow, or adequate vertebral body fill is accomplished. Unfortunately the optimal amount of vertebral body "fill" with cement may not have been achieved by the time extravasation is identified or imminent, and therein lies the objective of this invention, namely to be able to perform the vertebroplasty procedure with a substantially lower rate of cement extravasation, while providing more satisfactory/ complete vertebral body fill of cement.

Polymer-based surgical cement systems have been employed for many years in contemporary orthopedics. In particular, polymethylmethacrylate (PMMA) has emerged as one of the most popular biocompatible cement systems. Other systems used for bone reinforcement, such as, allograft and autograft tissue suffer from numerous disadvantages including; the possibility of disease transmission, availability and expense, and variability of the host response regarding union and repair and slower progression to bony healing with bony incorporation and consequential pain relief. More recently, osteogenic substances (BMP's) have been utilized for such purposes to induce healing of fractured bones, as well as to stabilize them acutely, like a cement.

Polymethylmethacrylate cement systems generally comprise two components; a monomer liquid (e.g., methylmethacrylate), and a dry powder component (e.g., polymethylmethacrylate (PMMA)). These two components are mixed together to begin the polymerization process and are placed inside the receiving site or cavity. The polymeric bone cement will then solidify (harden). Polymer-based bone cement is potentially toxic to the patient and extravasation of the cement has been linked to various clinical factors such as pulmonary embolism and compression of adjacent neural structures including the spinal cord occasionally necessitating emergency decompression surgery. Also extravasation through the fractured endplates into the adjacent disc may occur. Vertebral body cement extravasation is never desirable but rarely clinically significant, as has been shown in multiple clinical studies.

PRIOR ART

Although there is much information in the art regarding methods and devices intended to reinforce damaged and/or diseased bone, little of the art is concerned with arresting extravasation (leakage) of the cement from within the bone while creating a solidified cement having an essentially homogenous matrix for enhanced stability. What is needed in the art is an efficient method and kit which can safely achieve a homogenous cement matrix upon solidification in affected areas of the fracture and the surrounding, adjacent osteoporotic bone including the subchondral level, and with reduction or prevention of cement leakage through the fracture planes/channels and cancellous voids extending out through the cortical margins of the vertebral body. This provides fracture stability and pain reduction with increased cancellous bone support in these areas and reducing the possibility of further fracture and/or collapse.

U.S. Patent Publication No. 2006/0052743 to Reynolds relates to an improved vertebroplasty procedure for reducing embolisms, leakage, and cement loosening. The method includes preparing a vertebral body by directing a fluid into the open porosity of the porous cancellous bone structure to dislodge at least a portion of the soft tissue contained therein, then injecting bone paste into the exposed bone structure. Unlike the present invention, the Reynolds invention requires a device for removing the soft tissue debris, lest these dislodged emboli flow into the patient's bloodstream.

U.S. Patent Publication No. 2006/0122614 to Truckai et al., is drawn to medical devices and methods for restoring vertebral body height by controlling the geometry of fill material introduced into cancellous bone. The system utilizes RF energy in combination with a conductive bone fill material for polymerizing the surface of the inflow plume to control the geometry of the fill material and the application of force caused by inflows to fill material. In another embodiment, the system includes an energy source selectively couplable to the fill material to alter the viscosity of the fill material as it flows out of the introducer. Unlike the present invention, the medical devices and methods of Truckai et al., adjust the fill material viscosity to reduce leakage of the hardening material.

U.S. Pat. No. 6,726,691 to Osorio et al., discloses devices and methods for treating fractured and/or diseased bone. A first material, such as a bone filler (e.g. bone cement), is introduced into the cancellous bone of a damaged vertebral body. Next, an expandable structure is then inserted and expanded in the bone compressing this first material and/or cancellous bone, thereby creating a cavity and/or a barrier region of compressed cancellous bone, substantially surrounding the cavity. A second bone filler material is introduced into the same damaged vertebral body through the same insertion device. Thus, their first bone filler material requires the expandable device to compress (fracture) the surrounding cancellous bone of the fractured vertebra as a void is necessarily created to perform that procedure.

Although there are numerous publications and patents directed to bone treatment systems and methods that utilize bone cement to reinforce weakened and/or fractured bone, none of the aforementioned prior art have effectively addressed the problems outlined herein; specifically the problem of forming a homogenous or heterogeneous cement matrix by firstly injecting a flowable substance of particulate matter (radiopaque or non-radiopaque) to thereby produce a heterogeneous or substantially homogeneous particulate containing mixture which is dispersed within at least a portion of the bone cement, to prevent or restrict cement extravasation.

SUMMARY OF THE INVENTION

The instant invention provides an efficient method and kit for achieving enhanced reinforcement and stabilization in affected bony members by increasing material density inside the affected bone to prevent further fracture and/or collapse. The method is generally accomplished by carrying out three basic steps; providing a first flowable quantity of a bone cement in particulate form; providing a second flowable quantity of a bone cement in liquid form; and administering the first followed by or mixed with the second flowable quantities of bone cement into the interior cavity of a bone. In one illustrative, albeit non-limiting embodiment of the invention, it is required that the particulate and flowable bone cement is composed of the same material, albeit in solid and liquid form, so that the two components readily polymerize to form a homogenous cement matrix, in the end result. In a particularly preferred embodiment, the first flowable quantity of bone cement consists of solid polymerized particles of PMMA with a radiopaque marker substance and the second flowable quantity is comprised of liquid bone cement. The second flowable quantity includes at least the dry powder component and the liquid monomer (MMA) previously mixed together to form the polymerized PMMA cement.

In addition, either the first or second flowable quantity of bone cement may include additional components in amounts designed to react with the other flowable quantity of bone cement (e.g., particulates), if necessary, to form a homogenous solid cement matrix in situ. Examples of additional components include (albeit are not limited to) at least one initiator used to begin the solidification process, an accelerator that enhances the solidification process, and/or at least one stabilizer to inhibit the solidification process until the first and second flowable quantities of bone cement are disposed inside the interior cavity of the bony member.

Another embodiment of this invention utilizes flowable/injectable particles of a different material, namely a biocompatible and radiopaque material, which may include, but is not limited to Barium, Tantalum, or other ceramic or metallic substances or biological ones, allograft, autograft, tricalcium phosphates, etc. which are compatible with liquid bone cements, e.g. PMMA. These particulate, but flowable/injectable substances, are designed to act as occluding barriers to cement extravasation and can be of similar or dissimilar sizes and shapes to best occlude the cancellous fracture planes extending out of the vertebral body through the cancellous and cortical breaches and margins. They are injected through the cannula needle with a plunger, before the liquid bone cement or other stabilizing composite substance, functioning without any expandable device or other device or structure or balloon deployment being necessary. And the force of the higher pressure injection of the second liquid filler pushes and forces these larger particles into the fracture crevices and cracks and voids so that the resulting blockage or inhibition and restriction of liquid cement will reduce extravasation.

The instant invention also provides a kit for administration of the first and second bone cement material into the interior cavity of the bone. The kit is constructed and arranged for controlled deposition of the first and second bone cement material sequentially or simultaneously.

The instant invention is contemplated for use with any bone-related disease and/or defect which may involve thinning, fractured, weakened and/or damaged bones; illustrative, albeit non-limiting situations are, osteoporosis, after a traumatic injury to a vertebral body and/or limb with resultant osteopenia, corticosteroid regimens, bone damage due to radiation treatments, etc.

Accordingly, it is an objective of the instant invention to provide a method and kit for creating a homogenous cement matrix in situ, while reducing or eliminating extravasation of the bone cement.

Another objective of the present invention is to teach a method with a kit that may be utilized in concert with other procedures, non-limiting examples of which include, disk arthroplasty, vertebroplasty, KYPHOPLASTY, and other surgical methods which repair existing vertebral fractures.

Still another objective of this invention is to provide polymeric bone cement that does not raise a new material issue relative to the Federal Food and Drug Administration (FDA) and/or biocompatibility requirements.

A further objective of this invention is to provide a first flowable quantity of bone cement or other occluding fillers in particulate form. The particulates are radiopaque and able to be monitored using visualization equipment (X-ray, CT scanning equipment, MRI or the like). These particulates are notably flowable in the introducing cannula but occluding in the cancellous bone fracture channels and fracture planes. They may be injected by plunger or piston or trocar inserted into the outer cannula filled with the particulates. Alternatively the particulates may be injected into the cancellous fractured bone by the force of the second filler, the liquid form of the bone cement being injected.

Other objectives and advantages of the instant invention will become apparent from the following description taken in conjunction with the accompanying drawing(s) wherein are set forth, by way of illustration and example, certain embodiments of the instant invention. The drawing(s) constitute a part of this specification and include exemplary embodiments of the present invention and illustrate various objects and features thereof.

ABBREVIATIONS AND DEFINITIONS

Figure 1:
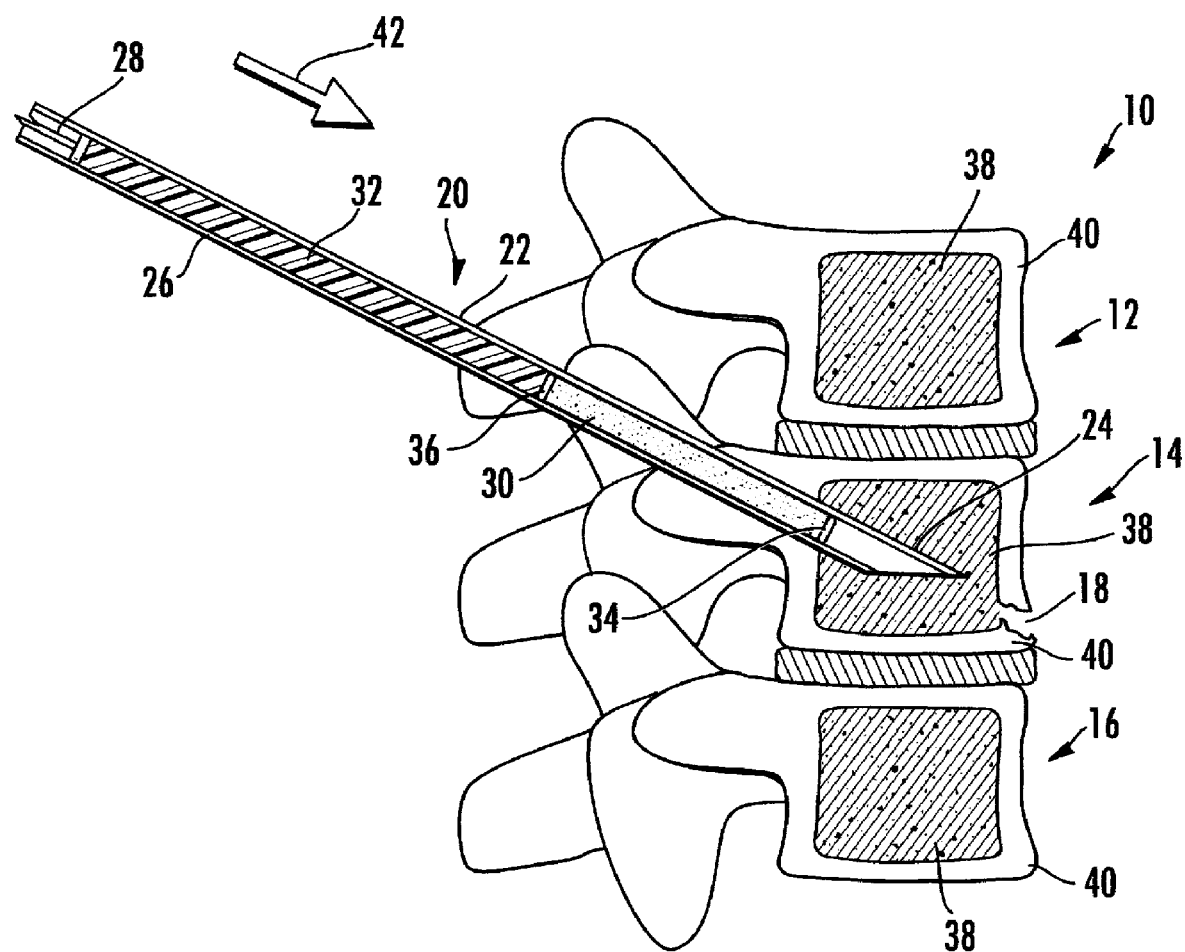
FIG. 1 is a schematic side view of a spine segment showing a fractured vertebra with a means for delivering the bone cement in communication with the interior cavity of the vertebra, in accordance with one embodiment of the invention.

The following list defines terms, phrases and abbreviations used throughout the instant specification. Although the terms, phrases and abbreviations are listed in the singular tense the definitions are intended to encompass all grammatical forms.

As used herein, the abbreviation "BMP" refers to bone morphogenetic protein. BMP's are signal transducting proteins of the transforming growth factor-beta superfamily which function in skeletal development and bone formation.

As used herein, the term "osteoplasty" refers to any surgical procedure or process by which total or partial loss of bone (vertebral, long bone, etc.) is remedied, illustrated by, albeit not limited to, KYPHOPLASTY and vertebroplasty.

As used herein, the term "initiator" refers to any component that may be added to either the first or second flowable quantity of the bone cement to initiate the polymerization process. One non-limiting example of a suitable initiator is benzyl peroxide.

As used herein, the term "stabilizer" refers to any component that may be added to either the first or second flowable quantity of the bone cement to prevent premature polymerization process. One non-limiting example of a suitable stabilizer is hydroquinone.

As used herein, the term "accelerator" refers to any component that may be added to either the first or second flowable quantity of the bone cement to increase the rate of polymerization. One non-limiting example of a suitable accelerator is N,N-dimethyl-p-toluidine.

As recited herein, the term "particulates" include, albeit are not limited to, filaments, microspheres, powders, granular elements, flakes, chips, tubules, cubes, triangles, regular and geometric shapes or irregular and randomly shaped, and the like.

As recited herein, the phrase "a bone cement" refers to an acrylic polymer composed of a first flowable quantity of solid polymerized particles of polymethylmethacrylate (PMMA) and a second flowable quantity which includes at least the dry powder component and the liquid monomer methylmethacrylate (MMA) previously mixed together to form a liquid. Either the first or second flowable quantity of the bone cement may include additional components (e.g., stabilizer, accelerator, initiator, etc.) in amounts designed to react with the other. The first or second flowable quantities of the bone cement solidify to form a substantially homogeneous solid cement matrix in situ.

As used herein, the phrase "a radiopaque material" refers to any biological and/or synthetic material which is capable of combination with bone cement. It can also be added (to the bone cement) in order to facilitate visualization of the administration of the bone cement by visualization equipment (X-ray, CT scanning equipment, MRI or the like.)

As used herein, the phrase "bone growth enhancing agent" refers to any biological and/or synthetic molecule or material which facilitates and/or increases the rate of bone growth and is capable of combination with bone cement.

DETAILED DESCRIPTION OF THE INVENTION

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

As discussed above, many deleterious effects accompany bone fracture, such as, pain, immobility, deformity, increases in length and cost of healthcare, and a general reduction in the quality of life of the individual suffering the fracture. The instant invention can alleviate these deleterious effects by providing a method and kit designed to introduce reinforcing bone cement to the interior cavity of the fractured bony member, thus preventing further fracture and/or collapse while mitigating extravasation of the bone cement which is potentially deleterious or even toxic to the patient.

The method and kit of the instant invention are equally suited to the treatment of vertebral bodies and/or long bones. Generally, the method is accomplished through carrying out three basic steps; providing a first flowable quantity of bone cement in particulate form, comprising radiopaque particulates of the same sizes and shapes or varied; providing a second flowable quantity of bone cement in a liquid form; and administering the first and second flowable quantities of bone cement into the interior (medullary) cavity of the bone. The first and second flowable material may be introduced into the interior cavity simultaneously or sequentially, as described further below.

Additionally, the instant invention provides a kit which includes a biocompatible delivery means for providing the first flowable quantity of bone cement in particulate form and other particulate substances as described and the second flowable quantity of bone cement in liquid form. The kit comprises the first flowable quantity of the bone cement in particulate form or other particulate substances; the second flowable bone cement in liquid form; and a means for delivering both the first and the second flowable bone cement within the interior cavity.

Figure 2:
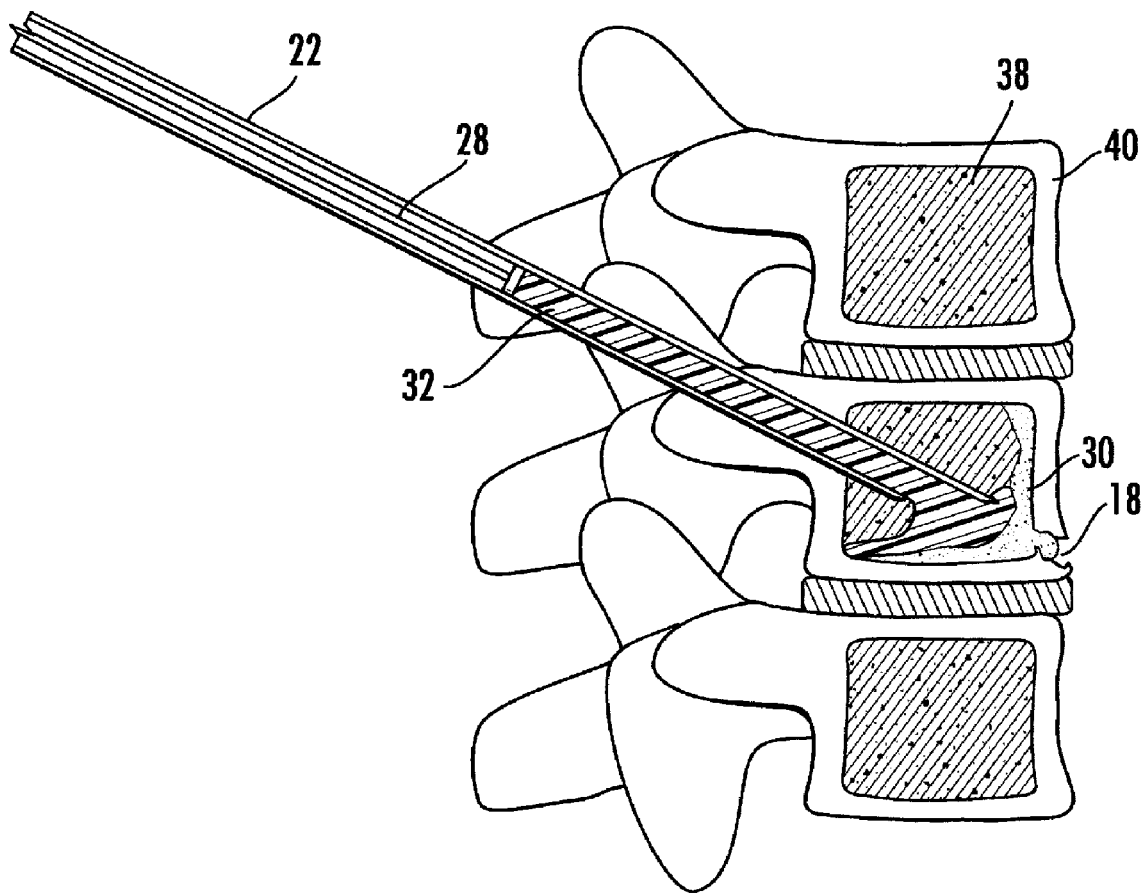
FIG. 2 is another side view the spine segment of FIG. 1, illustrating the means for delivering the first flowable component of the particulate bone cement particles into the interior cavity of the vertebra.
Figure 3:
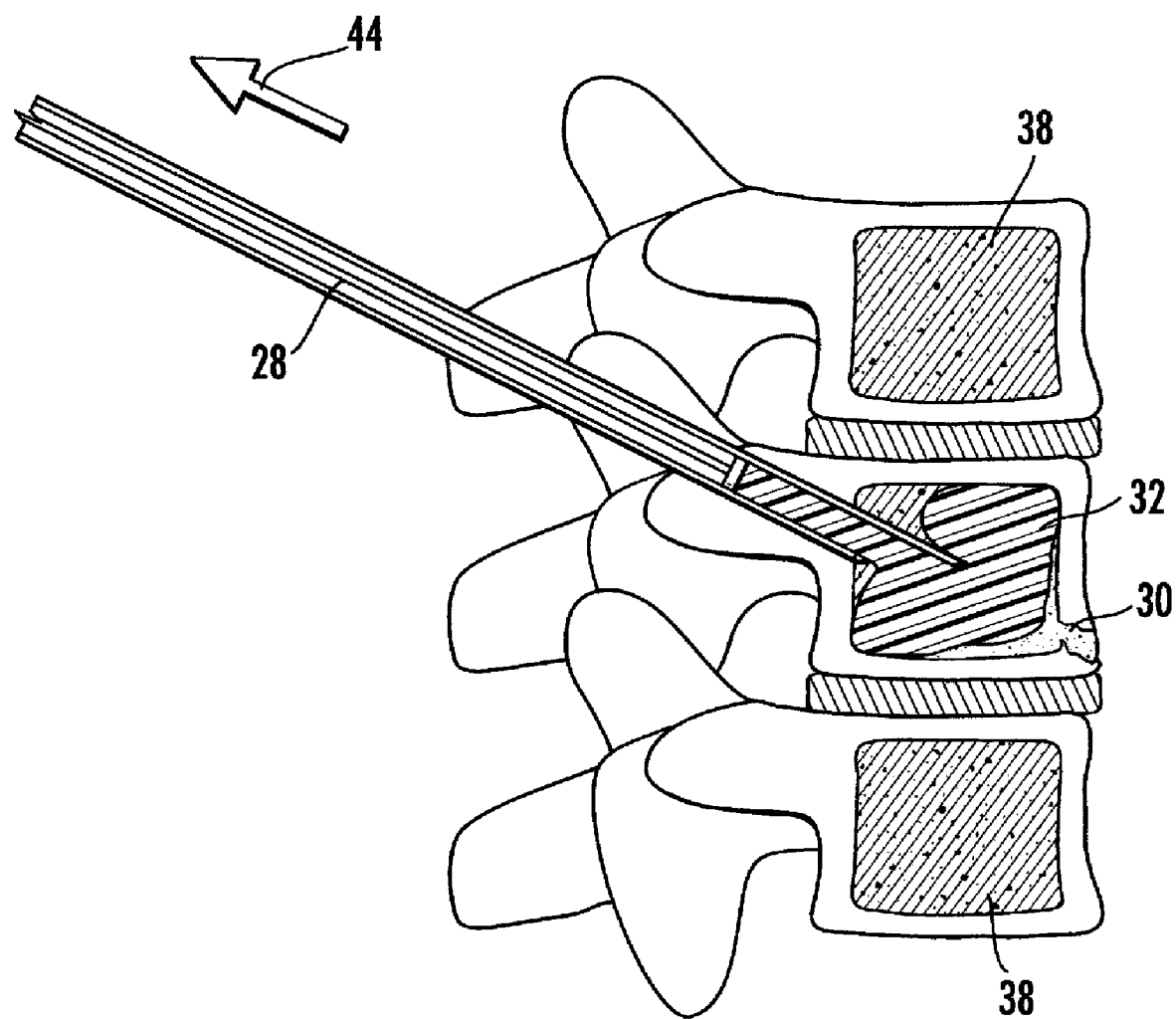
FIG. 3 is another side view of the spine segment of FIG. 1, illustrating insertion and subsequent removal of the means for delivering the first and second flowable components to the interior cavity of the vertebra.

Referring now to FIGS. 1-3, wherein like members are numbered consistently throughout, which illustrate a side view of a spine segment 10 showing multiple vertebra 12, 14, 16. Each vertebra includes an exterior formed from cortical bone 40 which encloses an interior cavity containing cancellous (spongy) bone 38. Vertebra 14 includes a source of extravasation 18 (crack, extended fracture plane, crevice, etc). The figures also illustrate a means for delivering 20 the bone cement in communication with the interior cavity of the vertebra through a trocar, cannula, or needle. The means for delivery is inserted by any suitable surgical procedure (e.g., transpedicular approach, etc.) Prior to the introduction of the needle, trocar or cannula, it is contemplated that the cancellous tissue within the interior bony cavity may or may not be substantially displaced or removed by any appropriate device, including a tamp, reamer, balloon catheter, or the like.

According to a preferred embodiment, the means for delivery is a cartridge having one chamber constructed and arranged for controlled deposition of the bone cement into the interior cavity of the bone. The form of the cartridge is illustrated here as having one hollow tubular shaft (e.g., needle, lumen, cannula). The size (volume, length, etc) of the cartridge will depend on the type, quality and density of bone being treated. The bone density may be predetermined using any suitable method, e.g., a standard bone density test. According to another embodiment, the means for delivery is a cartridge having a second chamber containing the second flowable bone cement, as described below.

The delivery means 20 has a sharp distal end 24 and a proximal end 26 in communication with at least one fluid displacement means 28. The fluid displacement means may be mechanical, electrical, or manual device capable of depositing both the first and second quantities of bone cement, or other particulate substances into the interior cavity. For example, the fluid displacement means may be a plunger (as depicted in the figures), or a trocar within a cannula, pump, or the like.

As further illustrated in FIG. 3, wherein arrow 44 is indicative of subsequent removal, a preferred embodiment is illustrated wherein the delivery means 20 is pre-loaded (by the manufacturer) with a first flowable quantity of bone cement in particulate form 30 and made of polymethylmethacrylate (PMMA) or other biocompatible particulate substances and which do not raise new material issues with the FDA. The particulates are dispensed at the distal end of the delivery means and the second flowable quantity of bone cement in liquid form 32 is introduced at the proximal end 26. The second flowable quantity of bone cement 32 may be prepared at the time of use by medical personnel by mixing the dry powder component of the PMMA and the liquid monomer, as described above. The second flowable quantity is then inserted into the proximal end of the delivery means at the time of use by any suitable means (e.g., syringe pump, etc), and the device is subsequently withdrawn after use.

The first flowable quantity of bone cement inside the delivery means 20 may be encapsulated by a rupturable membrane 34, 36 until needed by medical personnel, as shown in FIG. 1. The membrane is ruptured by actuation of the delivery means. The use of rupturable membranes prevent premature polymerization and solidification (hardening) of the bone cement inside the delivery means.

Alternatively, the delivery means may include a chamber pre-loaded with both the first flowable quantity of bone cement (particulates) and the second flowable quantity of bone cement (liquid bone cement), each may or may not be separated by a rupturable membrane (not shown) to prevent premature reaction there between. The liquid PMMA cement may in this case act as a dynamic plunger to displace the particulate matter (of whatever composition) ahead of it—down the cannula and into the cancellous bone thereby occluding the fracture cracks and crevices and reducing extravasation from within the vertebra.

Referring again to FIG. 1, the distal end of the cannula is inserted into an incision made in the tissue (including the cortical bone). Obviously, the incision must be of a width sufficient for insertion and maneuverability of the cartridge within the interior cavity of the bone. Bi-planar fluoroscopic or other image-guided systems may be used to guide the introduction of the cannula into the bone. The first flowable cement or other particulate substance may be forcefully injected into the fractured cancellous bone substance by the plunger or the trocar through the cannula to fill the fracture voids and cracks, occluding them and preventing or reducing the subsequently injected liquid bone cement from extravasation.

As discussed above, the distal end of the cartridge is sharp so that it may be easily guided through the cortical bone and into the interior cavity (direction shown by black arrow 42). The sharpened distal end provides for mechanical disruption of the cancellous tissue within the cavity. Upon activation of the fluid displacement means, the second liquid bone cement inside the cartridge is forced into contact with the first flowable quantity of particulate bone cement within the cartridge. The fluid force of the displacement means may be used to rupture the membranes between the first and second flowable quantities of bone cement.

FIG. 2 illustrates the particulates of the first flowable quantity of bone cement being forced into the vertebral body. The second flowable quantity of liquid bone cement is introduced into the cavity in an amount that substantially fills its entire volume causing the particulates of the first flowable quantity of bone cement to press against and displace the particles along the periphery of the interior cavity. The particles are further forced into or occlude any sources of extravasation, thereby substantially eliminating or reducing extravasation of the liquid cement from the interior cavity, see FIG. 3. As discussed above, surgical cement is potentially toxic and linked to various clinical factors. Once extravasation is prevented, the vertebral body can be pressure filled by controlled dispensing of the bone cement from the delivery means to optimally fill the vertebral body with liquid bone cement throughout the vertebral body from superior to inferior endplates, preventing further fracture of these areas, and to restore some of the height of the vertebra toward its pre-fractured height.

The distribution of the bone cement from the delivery means should always be carried out by controlled deposition. Controlling the deposition of the bone cement is necessary to assure that precise amounts of cement are distributed in a manner which avoids unintentional or additional fracture or extravasation.

Once inside the interior cavity, the second flowable quantity of bone cement polymerizes with the first flowable quantity of bone cement and solidifies over time, forming a homogenous cement matrix that provides interior reinforcement in order to prevent further fracture and/or collapse. If alternate filler particle substances are first used then they will be encased in the subsequent bone cement injected.

One cartridge design may not be ideally suited to every situation. As discussed above, it is contemplated herein that the delivery means may include two separate chambers, each chamber housing the first and second flowable quantity of bone cement, respectively. Each chamber is in communication with the interior chamber and may include a fluid displacement means (plunger, pump, or the like). This configuration allows for the simultaneous or sequential deposition of the first and second bone cement material into the interior cavity. The use of separate chambers ensures the two components (particulates, liquid cement) do not react prematurely.

Since the interior cavity volume the bone varies for each individual, the ratio of the first flowable of bone cement relative to the second flowable of bone cement may be decided on a per case basis since the quantity of the each depends on the length and interior volume of the bone to be treated, e.g. vertebral body, etc.

The post-procedure follow-up of the individual would include X-Rays and/or several bone density tests over a period of time in order to track the bone restoration in the treated vertebra.

The particulates of the first flowable quantity of bone cement may have a uniform particle size distribution or, preferably, a multiform particle size distribution. According to the multiform embodiment, the particle sizes may be loaded (by the medical personnel or the manufacturer) into the means for delivery in any size discriminated order or randomly distributed, as deemed suitable for the fracture. For example, larger sized particles may be disposed closer to the distal end of the cartridge, whereas smaller particles are disposed at the proximal end. As recited herein, the term "particulates" include (albeit are not limited to) filaments, microspheres, powders, granular elements, flakes, chips, tubules, cubes, pyramids and the like geometrical forms or randomly shaped particulates, and will be preferably be radiopaque or contain radiopaque substances for radiographic imaging by CT scanning or X-Ray or fluoroscopy.

Alternative embodiments would utilize bone growth materials in alternative vehicles or carriers in the form of a solution, suspension, controlled release formulation or the like present in either or both the first and second flowable quantity of cement. Other growth factors and/or bone growth accelerators may be added to the interior cavity via additional inserts and/or cannulas if desired.

Any natural and/or synthetic material which enhances bone growth is contemplated for use in the solution of the instant invention, illustrative, albeit non-limiting examples of such materials are BMP's, cytokines, hormones and growth factors. Illustrative, albeit non-limiting examples of BMP's are any of the fourteen types of human BMP's (BMP's 1-14). Cytokines are polypeptides transiently produced by many different types of cells and function as intercellular messengers, usually by binding to cell surface receptors. Illustrative, albeit non-limiting examples of cytokines are any of the interferons, tumor necrosis factors, lymphokines, colony-stimulating factors and erythropoietin. Hormones are also organic intercellular messengers. Illustrative, albeit non-limiting examples of hormones are steroid hormones, prostaglandins, peptide H, adrenalin and thyroxin. Growth factors are mitogenic polypeptides functioning in intercellular signaling. Illustrative, albeit non-limiting examples of growth factors are platelet derived growth factor, transforming growth factors and epidermal growth factor.

At least one radiopaque material can also be added (to the second flowable quantity of bone cement) in order to facilitate monitoring of the administration and distribution of the cement use visualization equipment (X-ray, CT scanning equipment, MRI or the like). Examples of suitable radiopaque components include, but not limited to, barium salts (e.g., barium sulfate, barium fluoride, barium polyacrylate), metal oxides (titanium dioxide, chromium oxide, zirconium oxide, chromium oxide, zinc oxide), bismuth glass and combinations thereof.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A kit for reducing or eliminating extravasation of liquid bone cement used to substantially reinforce an interior cavity of a bony member, comprising:
   a first flowable quantity of solid polymerized particles of bone cement;
   a second flowable quantity of a bone cement in liquid form, wherein the second flowable quantity includes at least a dry powder component and a liquid monomer previously mixed together to form a liquid, wherein said first or second flowable quantities of the bone cement solidify to form a substantially homogeneous solid bone cement matrix in situ; and a means for delivering said first and said second flowable bone cements within said interior cavity.

2. The kit of claim 1, wherein said means for delivering is a cartridge having a first chamber pre-loaded with at least said first flowable bone cement.

3. The kit of claim 2, wherein said means for delivering is a cartridge further including a second chamber containing said second flowable bone cement.

4. The kit of claim 1, wherein said particles are composed of polymerized polymethylmethacrylate.

5. The kit of claim 1, wherein said particles have a uniform particle size distribution.

6. The kit of claim 1, wherein said particles have a multi-form particle size distribution.

7. The kit of claim 1, wherein said bone cement further includes at least one bone growth enhancing agent.

8. The kit of claim 7, wherein said at least one bone growth enhancing agent is selected from the group consisting of bone morphogenetic proteins (BMP's), cytokines, hormones, growth factors and combinations thereof.

9. The kit of claim 1, wherein said bone cement further includes at least one radiopaque component.

10. The kit of claim 9, wherein said at least one radiopaque component is selected from the group consisting of barium salts, metal oxides, bismuth glass, tantalum, and combinations thereof.

11. The kit of claim 1, wherein said bone cement further includes an initiator for beginning a hardening process.

12. The kit of claim 11, wherein said bone cement further includes at least one accelerator for increasing the rate of said hardening process.

13. The kit of claim 1, wherein said dry powder component is composed of polymethylmethacrylate.

14. The kit of claim 1, wherein said liquid monomer component is composed of methylmethacrylate.

* * * * *